United States Patent [19]

Tavares et al.

[11] 4,067,906
[45] Jan. 10, 1978

[54] NOVEL PROCESS FOR THE SYNTHESIS OF TRICYCLO[6.2.2.0³,⁸]DODECANE DERIVATIVES

[75] Inventors: Robert F. Tavares, Cedar Grove, N.J.; Elliot Katten, New York, N.Y.

[73] Assignee: Givaudan Corporation, Clifton, N.J.

[21] Appl. No.: 711,321

[22] Filed: Aug. 3, 1976

[51] Int. Cl.² .................. C07C 43/00; C07C 49/48
[52] U.S. Cl. ...................... 260/586 G; 260/514 L; 252/522
[58] Field of Search ........... 260/586 R, 586 C, 586 F, 260/586 G, 514 L

[56] References Cited

U.S. PATENT DOCUMENTS

| | | | |
|---|---|---|---|
| 3,625,984 | 12/1971 | Levine et al. | 260/514 L |
| 3,681,470 | 8/1972 | Kitchens et al. | 260/586 R |
| 3,794,678 | 2/1974 | Dvonch et al. | 260/514 L |
| 3,988,366 | 10/1976 | Nagakura et al. | 260/586 F |

*Primary Examiner*—Norman Morgenstern
*Attorney, Agent, or Firm*—Thomas Cifelli, Jr.; Robert F. Tavares

[57] ABSTRACT

A novel process for the preparation of tricyclo[6.2.2.0³,⁸]dodecane derivatives is presented. This novel process is applied to the synthesis of the odorant 4-acetyl-1,7,7-trimethyltricyclo[6.2.2.0³,⁸]-3-dodecene, also known as 4-aceto-6,8a-ethano-1,1,6-trimethyl-1,2,3,5,6,7,8,8a-octahydronaphthalene.

6 Claims, No Drawings

NOVEL PROCESS FOR THE SYNTHESIS OF TRICYCLO[6.2.2.0³,⁸]DODECANE DERIVATIVES

BACKGROUND OF THE INVENTION

1. Field of the Invention

Tricyclo[6.2.2.0³,⁸]dodecanes

2. Prior Art

The fragrance industry relies heavily on the use of natural oils and products derived from natural oils in the preparation of their fragrance materials. There has, of course, been a constant trend toward the use of synthetic materials since they offer many advantages over the naturally derived products.

Synthetics are usually less dependent upon the vagaries of naturally derived products such as availability, price, quality, crop failure etc. and there is normally better control over their quality and reproducibility. In addition, naturally derived products are often complex mixtures in which one or two chemicals provide the major odor impact. If a feasible route toward the synthesis of the more important odor contributors exists, such odorants can be used in their own right free of the by-products which are indigenous to the oil.

There has been success in synthesizing a number of naturally derived compounds and such synthetics are commercially availble in large quantities. As the natural products become more complex in structure, however, the problem of a commercially feasible synthesis becomes more difficult. Consequently, many synthetic routes developed for natural products are of academic interest only inasmuch as they require reagents which are not readily availble, sophisticated techniques which do not readily lend themselves to to large scale production and, often, complex separations.

One product used in the perfume industry is obtained by applying an acetylation procedure (e.g. acetic anhydride + polyphosphoric acid) to the hydrocarbon fractions of American cedarwood oil which consist essentially of 40–50% α-cedrene, 5–10% β-cedrene and 40–50% cis thujopsene.

Kitchens et al. have shown that the most desirable odor components of the complex mixture obtained by acetylating American cedarwood oil are acetyl thujopsene derivatives [Garry C. Kitchens, Alan R. Hochstetler and Kent Kaiser, U.S. Pat. Nos. 3,678,119; 3,754,037; 3,681,470; 3,681,470; and Kitchens et al. J. Org. Chem. 37, 6 (1972) and J. Org. Chem. 37, 1 (1972)]. It was further disclosed in the above references that acetylation of pure (-)-thujopsene produced a product having a strong woody odor which upon analysis by gas chromatography revealed seven major components which were designated in order of elution as isomers A through G.

The major component, isomer G, constituted about half the mixture and possessed a powerful, woody, musk, ambergris odor far greater than that of any of the six other isomers. The structure of isomer G was shown to be 4-acetyl-1,7,7-trimethyltricyclo[6.2.2.0³,⁸]-3-dodecene, (1), (also known as 4-aceto-6,8a-ethano-1,1,6-trimethyl-1,2,3,5,6,7,8,8a-octahydronaphthalene) via an x-ray crystal structure determination on the ethylene thioketal derivative [Kitchens et al. J. Org. Chem. 37, 6 (1972)].

The overall conversion of cis-thujopsene to isomer G (1) is represented below.

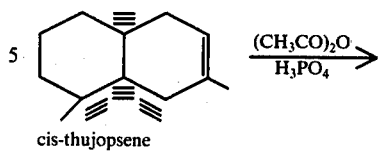

cis-thujopsene

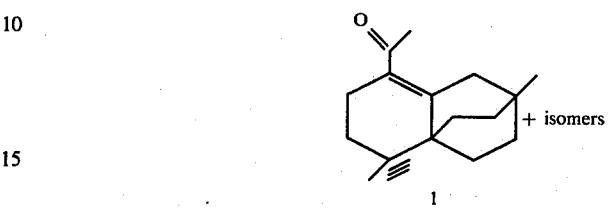

As readily apparent from the above, the conversion of cis-thujopsene to isomer G (1) involves complex rearrangements of the carbon skeleton which are explained in the reference. The only known methods of producing isomer G, (1), are those described in these references and all involve hydrocarbons derived from naturally occurring oils. Prior to this invention, there was no known way to synthesize the desired 4-acetyl-1,7,7-trimethyltricyclo[6.2.2.0³,⁸]-3-dodecene (isomer G) without relying on the naturally occurring oil.

It is also evident from a consideration of the known prior art that the isomer G, (1), is only one of a number of compounds produced from the acetylation of thujopsene and must be separated from these other compounds via sophisticated separation techniques before it can be provided in essentially pure form (i.e. >95% pure)

SUMMARY OF THE INVENTION

This invention provides a general process for the preparation of tricyclo[6.2.2.0³,⁸]dodecene derivatives such as the odorant 4-acetyl-1,7,7-trimethyltricyclo[6.2.2.0³,⁸]-3-dodecene (also known as 4-aceto-6,8a-ethano-1,1,6-trimethyl-1,2,3,5,6,7,8,8a-octahydronaphthalene or as 1-acetyl-7,10-ethano-4,4,7-trimethyl-1(9)-octalin and herein referred to as isomer G).

In its most general terms, the process of this invention allows the conversion of 4-arylbutanoic acid and substituted derivatives thereof to a tricyclo[6.2.2.0³,⁸]-dodec-9-en-4-one and substituted derivatives thereof. The resulting compound can be derivatized by known methods including catalytic hydrogenation to a tricyclo[6.2.2.0³,⁸]-dodecan-4-one which can be further converted to isomer G type compounds.

This novel sequence of steps is best illustrated by that used in the synthesis of isomer G which is shown in Scheme I.

Scheme I

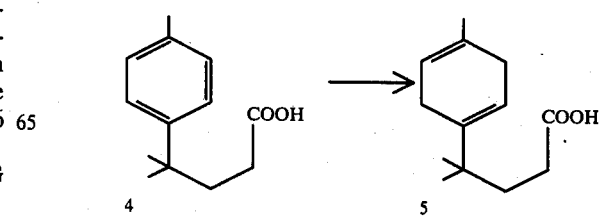

Scheme I-continued

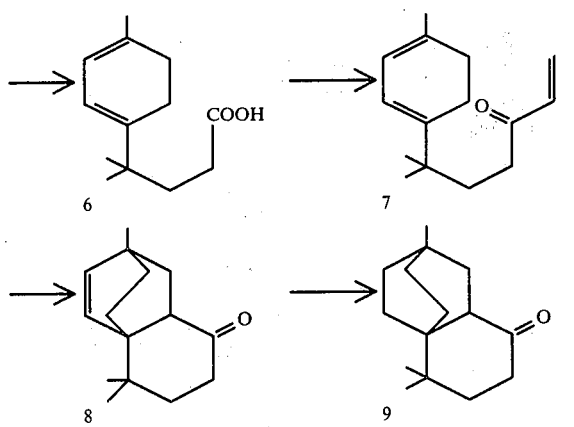

The acid at the beginning of this sequence can be prepared by known methods. The ketone at the end of the novel sequence can be converted to various derivatives, including isomer G, by known methods.

DESCRIPTION OF THE PREFERRED EMBODIMENTS

The novel sequence of steps disclosed herein includes a particularly novel intramolecular ring closure which provides the tricyclic [6.2.2.0$^{3,8}$]dodecane ring structure. While it is facile to provide a bicyclic [2.2.2]system via a normal intermolecular Diels-Alder reaction involving a 1,3-cyclohexadiene and a dienophile, the intramolecular counterpart is not. The probable reason is the problems presented in building, at the same time in the same molecule, a diene portion and a dienophile portion which would be at proper distances from one another to react.

It is far more simple to design two separate reactants which are to be brought together for the first time in a Diels Alder reaction than to have both groups in the same molecule prior to the Diels-Alder reaction. The reason for this is simply that both are reactive groups and once the first has been synthesized, the second must be introduced by using reactions that are compatible with the first.

Clearly, there were two major problems which had to overcome before the proposed sequence could be successful. The first was to introduce the requisite diene and dienophile at the appropriate place in the same molecule. The second problem was to hope that the conformation of the molecule would be such that the diene and dienophile groups would be properly disposed to one another and that they would properly react.

If the conformations were not favorable, if the equilibrium of the Diels-Alder favored the open rather than the closed compound or if the diene of one molecule preferred to react with the dienophile of another to form polymer, the synthesis would fail.

The novel sequence of steps provides a general synthetic route which allows the synthesis of a tricyclo[6.2.2.0$^{3,8}$]dodec-9-en-4-one. The resulting tricyclic ketone can be differently substituted by merely using an appropriately substituted 4-arylaliphatic acid or an appropriate vinyl organometallic. Such variations would be obvious to anyone experienced in the art based on the teachings of this invention.

It is preferred to illustrate this invention by reference to the particular series of reactions used in the preparation of isomer G with the equivalent sequences utilizing differently substituted reactants being understood. The total sequence used is shown in Scheme II which includes the inventive sequence going from 4 to 8.

Scheme II

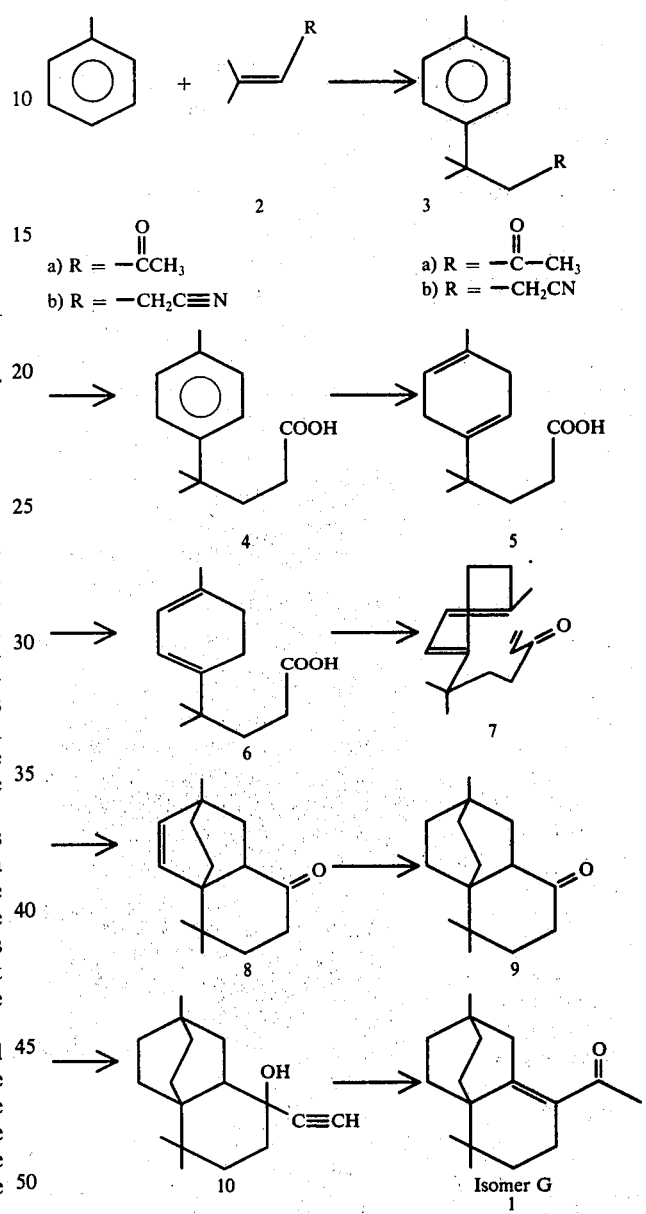

In the illustrated sequence of Scheme II, the acid 4 can be prepared by methods known in the art. The 4-methyl-4-p-tolylpentanoic acid had been prepared by Barnes and Buckwalter, J. Am. Chem. Soc. 73, 3858 (1951), via the ketone 3a utilizing a Willigerodt reaction. The overall yield from mesityl oxide (2a), toluene to the acid is on the order of about 20%. We prefer to use an alternate route via the 4-methyl-4-p-tolylpentanenitrile 3b in which the yields are several times higher. The 4-methyl-3-pentenenitrile (2b), prepared by the Knoevenagel condensation, is a known compound (J. P. Fluery and A. Bader, Bull. Soc. Chim. France, 1965, 951).

Other methods may be used to obtain the acid 4 and its analogs. It should be understood that the method by which 4 or its homologs and analogs is prepared is not critical to this invention. The chosen route to prepare 4 involves a Knoevenagel condensation between isobutyraldehyde and cyanoacetic acid to provide 2b, followed by a Friedel-Crafts reaction to provide 3b. The Knoevenagel reaction is well known and is reviewed in Vol. 15 of Organic Reactions (John Wiley and Sons Inc., New York). The advantage to this approach lies in the fact that one gets almost exclusively the $\beta, \gamma$-double bond and very little of the $\alpha,\beta$ double bond. (Alternate routes are available such as reacting prenyl chloride with cyanide).

The Friedel-Crafts reaction can be carried out in any of the known ways with any of the known catalysts. We prefer, however, to add aluminum chloride to a solution of the $\beta,\gamma$-unsaturated nitrile in toluene in portions at a temperature of $-10°$ C to $+20°$ C. Addition of aluminum chloride to the reactants gave higher distribution of the para-isomer (about 90% para and 10% meta). Other conditions, such as adding the nitrile to a mixture of toluene and aluminum chloride, or using higher temperatures seemed to give higher percentages of the meta isomer. The isomer ratio is not critical to this invention, however, because the by-products due to the meta isomer are removed in a later stage as will be shown.

The nitrile 3b is then converted to the acid 4 via a hydrolysis. Again, many methods are known in the art for converting nitriles to acids and the method chosen is not critical to this invention. We prefer to hydrolyze the nitrile with potassium hydroxide in refluxing glycol via a method similar to that described in Organic Synthesis, Coll. Vol. IV, page 95, John Wiley & Sons, Inc., New York, 1963. While this procedure gives high yields in a reasonable reaction time, other methods known in the art would also be applicable.

The 4-methyl-4-p-tolylpentanoic acid, 4, is converted to the novel intermediate 4-methyl-4(4-methyl-1, 4-cycloyhexadien-1-yl)pentanoic acid, 5, via the well known Birch reduction. The novel compound 5 can be made under any suitable Birch reaction conditions and these modifications and variations are well known and reviewed in the chemical literature and textbooks [e.g. A. J. Birch et al., Quart. Rev., 12, 17 (1958); H. O. House, "Modern Synthetic Reactions," pages 50–77, W. A. Benjamin, Inc., New York (1965)]. We prefer a method wherein a solution of the acid 4 in a suitable solvent, preferably THF, is added to refluxing liquid ammonia. An excess of lithium metal is added portionwise to the reaction mixture. The proton source was provided by adding ethanol. Again, the particular conditions under which this well known procedure is applied is not critical to this invention.

The novel 4-methyl-4(4-methyl-1,4-cyclohexadien-1-yl)pentanoic acid, 5, need not be isolated in its pure form, but can be converted directly to the novel 4-methyl-4(4-methyl-1,3-cyclohexadien-1-yl)pentanoic acid, 6, by methods known in the art. [See J. Am. Chem. Soc. 85, 3030 (1963).] We prefer to use the generally accepted method wherein the double bonds are isomerized into conjugation by means of potassium t-butoxide in a polar solvent such as dimethyl sulfoxide or dimethylformamide. Again, the conditions are not deemed to be critical.

The acid 6 need not be isolated in the pure form since, as will be shown, only the 1,3-diene will go on to the desired product of this reaction and any of the unconverted 1,4-diene, or products derived therefrom, will be separated at a later stage.

The acid 6 is converted into the ketone 7 by reacting with vinyl lithium. Organo lithium reagents are known to react with acids to provide ketones. (Margaret J. Jorgenson, "Organic Reactions" Vol. 18, Ch 1, John Wiley & Sons, Inc., New York; H. O. House and T. M. Bare, Org. Syn. 49, 81–5 (1969) and J. C. Floyd, Tetrahedron Letters 1974 (33), 2877–78).

The ketone 7 was not isolated in pure form. Although characteristic spectral features for 7 were noted in the crude reaction product, upon distillation they disappeared. Apparently, the internal Diels-Alder reaction occurred upon distillation of the crude material to provide the tricyclic ketone —8 (a mixture of exo and endo 1,7,7-trimethyltricyclo[6.2.2.0$^{3,8}$]dodec-9-en-4-one). The assignment of structure here is based primarily upon the fact that the mixture of ketones 8 was converted to the known compound 9 which was eventually converted to 1 whose structure was known with absolute certainty.

Fortuitously, the major product was the one desired and crystallized selectively from the complex mixture of isomers. The expected problems with nondesired tricyclo derivatives did not occur. (For example, it was possible that acid impurities, expected to be in the reaction mixture, would complicate a proposed separation of the desired product. It was known that meta impurity was carried along from earlier steps, yet there was no evidence of tricyclics derived from such products. It was also expected that possible 1,3-diene impurities having no substitution at the terminal carbons could react preferentially, but there was no evidence for this.)

The key step, the novel internal Diels-Alder reaction to provide a tricyclo [6.2.2.0$^{3,8}$] dodecane derivative, appears to be a facile and favored reaction.

The heart of this invention is in the novel sequence of steps used to accomplish the synthesis. Other routes attempted, too numerous to mention here, did not succeed because the critical intermediate having both a diene and a dienophile in the same molecule could not be prepared, or because a critical intermediate did not survive certain reaction conditions.

Each step in the novel sequence of reactions used is a reaction of known type. From the teachings and examples herein, coupled with the teachings available in the art, it would be within the scope of one skilled in the art, knowing that the basic reaction is successful, to vary the conditions to optimize yields or to apply the teachings to analogous systems. The invention here is in providing the novel sequence of steps by which the method is successful.

Both the exo and the endo 1,7,7-trimethyltricyclo[6.2.2.0$^{3,8}$]dodec-9-en-4-one, 8a and 8b are hydrogenated to the same ketone, the 1,7,7-trimethyltricyclo[6.2.2.0$^{3,8}$]dodecan-4-one, 9, reported by Kitchens et al. The ketone, 9, can then be converted to the known odorant 1 by methods disclosed in the art. (See H. U. Daeniker, A. R. Hochstetler, K. Kaiser, G. Kitchens, J. Org. Chem., 37, 1, 1972).

Illustration of the Preferred Embodiments by Examples

This invention discloses a novel method of preparing tricyclo [6.2.2.0$^{3,8}$]dodecane derivatives. This novel method is illustrated herein by applying it to the synthesis of the prized odorant 4-acetyl-1,7,7-trimethyltricyclo[6.2.2.0$^{3,8}$]-3-dodecene (also known as 4-aceto-6,8a-ethano-1,1,6-trimethyl-1,2,3,5,6,7,8,8a-octahydronaphthalene).

For purposes of illustration and completeness, each step of the total synthesis is set forth in a detailed example. These examples set forth the best conditions contemplated by us at this time, but should not be construed as being limited to the conditions set forth. The invention is a general process for preparing tricyclo [6.2.2.0$^{3,8}$] dodecane derivatives and is intended to embrace any equivalents or obvious variations which are known or should be known to a person skilled in the art.

Unless otherwise indicated, weights are in grams, temperatures are in degrees centigrade, pressures are in mm Hg, yields are given in percent theory, infrared spectra (ir) are reported in inverse centimeters (cm$^{-1}$), nuclear magnetic resonance spectra (nmr) (recorded as solutions in chloroform-d) are in δ units relative to tetra methylsilane (0.0δ), molecular weights were determined on a mass spectrometer, gas liquid chromatography data was obtained using a 10% Carbowax 20M (6 ft. × ¼ inch) column and/or a 10% SE 30 (6 ft. × ¼ inch) column and ultraviolet spectra were run in ethanol and reported in nanometers (nm).

EXAMPLE I

This example illustrates the preferred method for the preparation of the 4-methyl-4-p-tolylpentanoic acid.

A. Preparation of 4-methyl-3-pentenenitrile (2b)

Isobutyraldehyde (158 g, 2.2 mol), cyanoacetic acid (170 g, 2.0 mol), ammonium acetate (6.0 g, 77.7 m mol) and benzene (150 ml) were refluxed until the theoretical amount of water had separated in a Dean-Stark trap. Solvent was then removed atmospherically. Until the reaction temperature reached 100° C, pure solvent distilled. The distillation was continued and the temperature in the reaction vessel rose from 100° to 175° C. During this period, carbon dioxide was evolved and the crude product distilled. This crude product was then washed with sodium carbonate and distilled to yield 120.7 g (63.5%) of nitrile 2b. Physical properties and spectral data were consistent with the structuure and those reported in the literature [J. P. Fleury and A. Bader, Bull. Soc. Chim. France, 951 (1965)].

B. Preparation of 4-methyl-4-p-tolylpentanenitrile (3b)

Aluminum chloride (100 g, 0.75 mol) was added slowly (30 minutes) to a solution of 4-methyl-3-pentenenitrile (61.7 g, 0.65 mol) in toluene (300 ml) while maintaining the temperature below 10° C. After stirring an additional 4.0 hours at a temperature below 10° C, the mixture was poured onto an ice, water mixture containing 100 ml of 10% hydrochloric acid. The organic layer was washed (10% Na$_2$CO$_3$ then H$_2$O), concentrated and distilled to yield 94.8 g (78.5%) of 4-methyl-4-p-tolylpentanenitrile (3b) which was 91% the para isomer and 9% meta isomer (glc, 20M): bp 129° (1 mm); n$_D^{20}$ 1.5145; δ$_{TMS}^{CDCl_3}$ 7.13 (s, 4), 2.28 (s, 3) 1.95 (s, 4); 1.28 (s,6).

Anal. calcd. for C$_{13}$H$_{17}$N: C, 83.37; H, 9.15. Found: C, 83.27; H, 9.16.

C. Preparation of 4-methyl-4-p-tolylpentanoic acid (4)

Potassium hydroxide (112 g) is slowly dissolved (heat evolved) in ethylene glycol (400 ml) in a 2 liter copper (or stainless steel) flask. The 4-methyl-4-p-tolylpentanenitrile (94 g, 0.5 mol) was then added, the mixture refluxed for 6 hours, cooled to 10° C and diluted with 400 ml ice cold water. Hydrochloric acid (conc., 180 ml) was added slowly (heat evolved, cooling required) until the reaction mixture was acid to congo test paper. The resulting mixture was extracted with benzene, washed with water, concentrated and distilled to yield 92.8 g (89.6%) of the 4-methyl-4-p-tolylpentanoic acid: bp 178° (2 mm); n$_D^{20}$ 1.5147;

Anal. calcd. for C$_{13}$H$_{18}$O$_2$: C, 75.69; H, 8.80. Found: C, 75.70; H, 8.97.

Ir and nmr were consistent with the structure.

EXAMPLE II

Preparation of 4-methyl-4(4-methyl-1,4-cyclohexadien-1yl)-pentanoic acid (5)

To a refluxing solution of 4-methyl-4-p-tolylpentanoic acid (51.5 g, 0.25 mol) in tetrahydrofuran (500 ml) and liquid ammonia (1500 ml) was added, portionwise, lithium metal (26.0 g, 3.75 gram atom). After the reaction mixture was stirred for 15 minutes, ethanol (150 ml) was added over 40 minutes. The reaction mixture was stirred an additional hour until the dark blue solution became colorless. Ammonium chloride (50 g) was added and the ammonia allowed to evaporate. The residue was acidified with HCl (pH ca. 3), extracted with ethylene dichloride, washed with water, concentrated and distilled to yield 49.6 g (80.8%) of the 4-methyl-4-(4-methyl-1,4-cyclohexadien-1-yl)pentanoic acid: bp 128°–130° C (1 mm); n$_D^{20}$ 1.4955; λmax 211 nm; δ$_{TMS}^{CDCl_3}$ 11.21 (s,1), 5.43-5.50 (broad band, 2) 2.62 (s,4), 1.66 (s,3) 1.03 (s, 6H).

Anal calcd for C$_{13}$H$_{20}$O$_2$: C, 74.96; H,9.68. Found: C, 75.02; H, 9.85.

EXAMPLE III

Preparation of 4-methyl-4(4-methyl-1,3-cyclohexadien-1-yl)pentanoic acid (6)

A mixture of 4-methyl-4(4-methyl-1,4-cyclohexadien-1-yl)pentanoic acid (45.3 g, 0.22 mol), potassium t-butoxide (102 g, 0.91 mmol), toluene (110 ml) and dimethyl sulfoxide (1,000 ml) was stirred for 24 hours at room temperature. The solution was cooled, brought to neutral pH with hydrochloric acid, poured into 2 liters saturated sodium chloride, and extracted with methylene chloride. After the solution was washed with saturated sodium chloride solution and the solvent removed, the residual oil was distilled to yield 41.3 g (65.2%) of the 4-methyl-4(4-methyl-1,3-cyclohexadien-1-yl) pentanoic acid: bp 136°–138° (1 mm); n$_D^{20}$ 1.5029; δmax 264 nm; δ$_{TMS}^{CDCl_3}$ 11.15 (s,1), 5.62 (s,2), 2.06 (s,4) 1.78 (s,3), 1.05 (s,6).

Anal. calcd. for C$_{13}$H$_{20}$O$_2$: C, 74.96; H, 9.68. Found: C, 75.15; H, 9.62.

EXAMPLE IV

Preparation of 1,7,7-trimethyltricyclo[6.2.2.0$^{3,8}$]dodec-9-en-4-one (8)

A mixture of freshly distilled dimethoxyethane (250 ml), lithium hydride (880 mg, 110 mmol) and 4-methyl-4(4-methyl-1,3-cyclohexadien-1-yl)pentanoic acid was refluxed under Argon for 2.5 hours. The mixture was then cooled to 5° C and vinyl lithium in THF (111 g, 130 ml, 208 mmol) was added over a ten minute period. After stirring for an additional 5 minutes, the mixture was quenched by siphoning into a vigorously stirring solution of 28 ml of conc. HCl in 400 ml ice water. The aqueous layer was saturated with sodium chloride, and extracted with methylene chloride. The methylene chloride solution was washed (5% NaOH, 10% NaCl) and then concentrated. The product was crystallized from hexane to yield 7.5 g (40%) of the 1,7,7-trimethyltricyclo[6.2.2.0$^{3,8}$]dodec-9-en-4-one (8). Analysis by gas liquid chromatography and thin layer chromatography showed this to be a mixture of two isomers.

A sample of this mixture of ketones (1.0 g), which was 32.4% of one isomer and 61.8% of the other isomer, was chromatographed on 200 g of activated silica gel using a nine to one mixture of hexane-diethyl ether. There was obtained a clean separation of isomers yielding 318 mg of one isomer and 566.5 mg of the second isomer.

The first isomer was assigned structure 8a, hereinafter referred to as the exo isomer, based on spectral analysis: mp 105°-6° C; $\delta_{TMS}^{CDCl_3}$ 6.16 (q,2), 1.33 (s,3), 1.14 (s,3), 1.02 (s,3): mol. wt. 218.

Anal calcd. for C$_{15}$H$_{22}$O: C, 82.51; H, 10.16. Found: C, 82.50; H, 10.32.

The other isomer was assigned structure 8b, herein referred to as the endo isomer. Mp 67°-8° C, nmr $\delta_{TMS}^{CDCl_3}$ 5.97 (q,2) 1.24 (s,3), 1.17 (s,3), 1.05(s,3) mol. wt. 218.

Anal calcd. for C$_{15}$H$_{22}$O: C, 82.51; H, 10.16. Found: C,82.44; H, 10.30.

EXAMPLE V

Preparation of
1,7,7-trimethyltricyclo[6.2.2.0$^{3,8}$]dodeca-4-one (9)

The 1,7,7-trimethyltricyclo[6.2.2.0$^{3,8}$]dodec-9-en-4-one (6.1g, 28.0 mmol) was hydrogenated at room temperature in methanol (250 ml) over 5% palladium on carbon (0.3g) at a pressure of 50 psi. The catalyst was filtered, the solvent removed and the residual oil distilled to yield 5.6 g (92%) of the 1,7,7-trimethyltricyclo[6.2.2.0$^{3,8}$]dodeca-4-one: mp 51.5°-52.5°; $\delta_{TMS}^{CDCl_3}$ 1.16 (s,3), .86 (s,3), .81 (s,3); mol. wt. 220.

Anal. calcd. C$_{15}$H$_{24}$O: C, 81.76; H, 10.98. Found: C, 82.03; H, 10.90.

EXAMPLE VI

Preparation of
4-Ethynyl-1,7,7-trimethyltricyclo[6.2.2.0$^{3,8}$]-4-dodecanol (10)

The system was purged with an inert gas (Argon) to remove air.

To dry 1,4-dioxane (45 ml) saturated with acetylene was added lithium acetylide-ethylene diamine complex (3.0 g, 30 mmol). The 1,7,7-trimethyltricyclo[6.2.2.0$^{3,8}$]-dodeca-4-one (2.8 g, 12.7 mmol) dissolved in dry dioxane (30 ml) was slowly added over a 1 hour period at 15° C. The mixture was stirred for 4 hours, poured into saturated ammonium chloride solution and extracted with diethyl ether. The solvent was removed and the residual oil distilled to yield 2.7 g of product which was a mixture of ethynyl alcohol and starting material. The ethynyl alcohol was easily removed from the starting material via column chromatography (350 g of grade 3 alumina) using a mixture of 10% ether, 90% hexane as the eluting solvent. There was provided 1.7 grams (53%) of pure ethynyl alcohol; ir 3450-3550 (broad —OH), 3310 cm$^{-1}$; $\delta_{TMS}^{CDCl_3}$ 2.33 (s,1), .87(s,3), .80(s,3) .77 (s,3).

Anal. calcd. for C$_{17}$H$_{26}$O: C, 82.87, H, 10.64. Found: C, 82.92; H, 10.73.

EXAMPLE VII

Preparation of
4-acetyl-1,7,7-trimethyltricyclo[6.2.2.0$^{3,8}$]-3-dodecene

The 4-ethynyl-1,7,7-trimethyltricyclo[6.2.2.0$^{3,8}$]-4-dodecanol (.54 g, 2.2 mmol) was added to 82% formic acid (2.0 ml) and the mixture refluxed for two hours. The reaction mixture was poured into water, extracted with diethyl ether, concentrated and distilled affording .466 g of a mixture which was 68.6% 4-acetyl-1,7,7-trimethyltricyclo[6.2.2.0$^{3,8}$]-3-dodecene. (53.5% theory). The mixture was chromatographed through 100 g of silica gel to yield a pure sample of 4-acetyl-1,7,7-trimethyltricyclo[6.2.2.0$^{3,8}$]-3-dodecene. The product was identical to that isolated by Kitchens et al., supra.

We claim:

1. The process for the preparation of 1,7,7-trimethyltricyclo[6.2.2.0$^{3,8}$]dodec-9-en-4-one from 4-methyl-4-p-tolylpentanoic acid which comprises:
    a. 1,4-hydrogenating the aromatic ring of the 4-methyl-4-p-tolylpentanoic acid via a Birch reduction to 4-methyl-4(4-methyl-1,4-cyclohexadien-1-yl)pentanoic acid;
    b. isomerizing the 4-methyl-4(4-methyl-1,4-cyclohexadien-1-yl)pentanoic acid to 4-methyl-4(4-methyl-1,3-cyclohexadien-1-yl)pentanoic acid in the presence of a base;
    c. reacting the 4-methyl-4(4-methyl-1,3-cyclohexadien-1-yl)pentanoic acid with vinyl lithium to form the intermediate 6-methyl-6(4-methyl-1,3-cyclohexadien-1-yl)hepten-3-one which is converted via an internal Diels-Alder reaction to form the 1,7,7-trimethyltricyclo[6.2.2.0$^{3,8}$]dodec-9-en-4-one.

2. The process of claim 1 wherein the 4-methyl-4-p-tolylpentanoic acid is 1,4 hydrogenated via a Birch reduction utilizing lithium or sodium as the alkali metal, liquid ammonia as the solvent and an alkanol as the proton source.

3. The process of claim 2 wherein the 4-methyl-4(4-methyl-1,4-cyclohexadien-1-yl)pentanoic acid is isomerized in the presence of potassium tertiary butoxide.

4. 1,7,7-Trimethyltricyclo[6.2.2.0$^{3,8}$]dodec-9-en-4-one, an intermediate of claim 1.

5. The endo isomer of claim 4.

6. The exo isomer of claim 4.

* * * * *